(12) United States Patent
Malakouti et al.

(10) Patent No.: US 6,802,353 B2
(45) Date of Patent: Oct. 12, 2004

(54) APPARATUS FOR RECYCLING WASTE FROM AN ABSORBENT ARTICLE PROCESSING LINE

(75) Inventors: Nezam Malakouti, Loveland, OH (US); James Harold Davis, Amelia, OH (US); Alan Christopher Pattillo, Dover, DE (US); Terrill Alan Young, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 221 days.

(21) Appl. No.: 10/266,227

(22) Filed: Oct. 8, 2002

(65) Prior Publication Data

US 2003/0066594 A1 Apr. 10, 2003

Related U.S. Application Data

(60) Provisional application No. 60/328,211, filed on Oct. 10, 2001.

(51) Int. Cl.[7] .............................................. B32B 7/00
(52) U.S. Cl. ...................... 156/433; 156/510; 156/92; 264/37.28
(58) Field of Search .................... 156/433, 94, 167, 156/168, 180, 181, 176, 178, 510; 264/37.28, 37.3, 37.32

(56) References Cited

U.S. PATENT DOCUMENTS

| | | | |
|---|---|---|---|
| 5,019,311 A | 5/1991 | Koslow | |
| 5,147,722 A | 9/1992 | Koslow | |
| 6,163,943 A | 12/2000 | Johansson et al. | |
| 6,319,342 B1 | 11/2001 | Riddell | |
| 6,475,315 B1 * | 11/2002 | Kean et al. | 156/62.2 |

FOREIGN PATENT DOCUMENTS

| | | |
|---|---|---|
| EP | 0 788 336 B1 | 8/1997 |
| EP | 1 215 325 A1 | 6/2002 |
| WO | WO 99/45186 | 9/1999 |
| WO | WO 01/26592 A1 | 4/2001 |
| WO | WO 02/49685 A2 | 6/2002 |
| WO | WO 02/50347 A1 | 6/2002 |
| WO | WO 02/083049 A1 | 10/2002 |
| WO | WO 02/083050 A1 | 10/2002 |
| WO | WO 02/083051 A1 | 10/2002 |
| WO | WO 02/083805 A1 | 10/2002 |
| WO | WO 02/084021 A1 | 10/2002 |

OTHER PUBLICATIONS

Artec Maschinenbau Ges.m.b.H./Austria. The Artec Recycling Machine (Large Image). From the Internet: http://www.artec.co.at/dieartee.htm. 2 pages.

* cited by examiner

Primary Examiner—Blaine Copenheaver
Assistant Examiner—Barbara J. Musser
(74) Attorney, Agent, or Firm—Jack I. Oney, Jr.; Michael S. Kolodesh; Jay A. Krebs

(57) ABSTRACT

A production line for manufacturing disposable absorbent articles from bulk starting polymeric materials including virgin and on-line recycled polymeric materials. The production line includes a continuous process that links the steps of forming the webs with the steps of converting the webs into disposable absorbent articles. The production line recycles non-woven materials produced on the production line back into the production process of producing disposable absorbent articles. The recycling operations can also include a spun-bonded recycling and a melt-blown recycling. The production line can be a single-product-lane operation or a multiple-product-lane operation.

14 Claims, 10 Drawing Sheets

APPARATUS FOR RECYCLING WASTE FROM AN ABSORBENT ARTICLE PROCESSING LINE

This application claims the benefit of U.S. Provisional Application No. 60/328,211, filed Oct. 10, 2001.

FIELD OF THE INVENTION

The present invention relates to a production line for manufacturing disposable absorbent articles from bulk starting polymeric materials including virgin and on-line recycled polymeric materials.

BACKGROUND

Disposable absorbent articles are often produced on high-speed converting lines using, for starting materials, continuous webs of fabrics, films, foams, elastics, etc. that have been transported from web producers in a packaged form (e.g., as wound rolls or festooned boxes), and are unpacked (e.g., unwound or de-festooned) in order to be fed as continuous webs into the converting line. In the converting lines, various converting operations work the webs to convert them into components of disposable absorbent articles that are eventually joined into a composite web that is finally cut into discrete final articles.

Unfortunately, packing and transporting continuous webs presents several problems. First, packing and transporting can often irreversibly change the web material, especially the webs that need to retain original, pre-packaged properties. For example, a soft, high-loft web can become continuously flat as a result of roll winding or intermittently deformed as a result of festooning. (When wound into a roll, the web is subjected to compression forces that are often needed for both retaining the web in the roll formation and for subsequent un-winding of the web from the roll. Also, when packaged in a festoon configuration into a box, the web often develops a permanent creep in the folded portions of the festooned web due to being bent and compressed.) Second, webs often need to be provided with special strength properties to make them suitable for roll winding or festooning. These properties often are achieved by applying to these webs special additives that can affect or compromise the desired properties of the final product and/or increase the cost of the web. Similar negative effects can take place when, prior to roll winding, the webs are sprayed with anti-static solutions to prevent or minimize in-layer subsequent sticking during un-winding of the web. Third, webs often require relatively expensive winding and un-winding high-speed automatic equipment and qualified personnel to operate and support it. Fourth, often the material properties that cannot be provided by a packaged web need to be provided by converting operations specially developed to make the web softer, thinner, thicker, elastic, absorbent, cloth-like, breathable, aesthetic, etc. These operations add more cost and time in developing new products.

Consequently, it would be beneficial to reduce or eliminate the need for packing and transporting of the webs to the product converting lines by providing a new process which is continuous from the material-forming operations to the product-converting operations. Further, because the web-forming operations need to run continuously without interruptions in order to prevent solidification of molted polymeric materials inside of the web-forming equipment, and the product-converting operations may have interruptions or production outages due to various malfunctions, it would be beneficial for the new process to recycle the polymeric materials produced by the web-forming operations during the production outages. It would be further beneficial to re-use the recycled materials in the new process.

SUMMARY OF THE INVENTION

In response to the difficulties and problems discussed above, a new production line for manufacturing disposable absorbent articles has been discovered that can reduce or eliminate the need for packaged webs. The production line includes a continuous process that links the web-forming operations, specifically nonwoven-web forming operations, with the product-converting operations. The production line utilizes bulk starting polymeric materials, both virgin polymeric materials and polymeric materials recycled and on the production line to be re-used on the production line in production of disposable absorbent articles. The production line can be a single-product lane operation or a multiple-product lane operation.

In one aspect, the present invention concerns a production line that extrudes polymeric materials and forms individual components from the extruded materials, such as a liquid previous topsheet, a liquid impervious backsheet and an absorbent core disposed therebetween. The production line includes a moving surface to move a web of material through the production line; a backsheet station adjacent the moving surface to form the backsheet by extruding a first polymeric material, provided to the backsheet station as a first starting material, onto the moving surface; a core station adjacent the moving surface to form the absorbent core by extruding a second polymeric material, provided to the core station as a second starting material, onto the moving surface; and a topsheet station adjacent the moving surface to form the topsheet by extruding a third polymeric material, provided to the topsheet station as a third starting material, onto the moving surface.

The production line further includes one or more cutting devices adjacent the moving surface to cut a trim and to form lateral configurations of the topsheet and the backsheet. The production line further includes a first recycling station for collecting and recycling the trim into the first recycled material and a second recycling station for collecting and recycling non-woven materials of the topsheet, the backsheet or the absorbent core collected during an outage of the production line into a second recycled material. The production line further includes one or more bonding modules adjacent the moving surface to provide the second recycled material for bonding the backsheet, the topsheet and the absorbent core to each other.

In another aspect, the present invention concerns a production line that extrudes and forms the topsheet and the backsheet from the extruded polymeric materials and combines these components with an absorbent core produced off the production line and provided to the production line as a continuous web or discrete objects. The production line further includes one or more cutting devices adjacent the moving surface to cut a trim and to form lateral configurations of the topsheet and the backsheet. The production line further includes a recycling station for collecting and recycling the trim and non-woven materials of the topsheet or the backsheet into a recycled material. The production line further includes one or more bonding modules adjacent the moving surface to provide the recycled material for bonding the backsheet, the topsheet and the absorbent core to each other.

In another aspect, the present invention concerns a method for recycling continuous fibers exiting one or more spun-bonded modules during an outage of the production line. The method includes the following steps: (a) providing at least one spun-bonded module; (b) diverging the continuous fibers exiting the spun-bonded module into a recycling operation by a gust of a compressed fluid; (c) disintegrating the continuous fibers in the recycling operation; (d) conveying the disintegrated fibers into a recycling station; and (e) recycling the disintegrated fibers into a recycled polymeric material.

In another aspect, the present invention concerns a method for recycling a molten polymeric material exiting a spinneret of a melt-blown module back in the melt-blown module, the method includes the following steps: (a) providing the melt-blown module extruding the molten material; (b) providing a collecting die for collecting the molten polymeric material from the spinneret; (c) providing a conduit being in communication with the collecting die for transporting the molten polymeric material; (d) collecting the molten polymeric material exiting the spinneret by the collecting die; and (e) transporting the molten polymeric material by the conduit from the collecting die to a metering pump of the melt-blown module for re-extruding the molten polymeric material through the spinneret.

BRIEF DESCRIPTION SHOWN IN THE DRAWINGS

The present invention will be more fully understood and further advantages will become apparent when reference is made to the following detailed description of the invention and the accompanying figures. The figures are merely representative and are not intended to limit the scope of the appended claims.

DETAILED DESCRIPTION OF THE INVENTION

Figure 1:
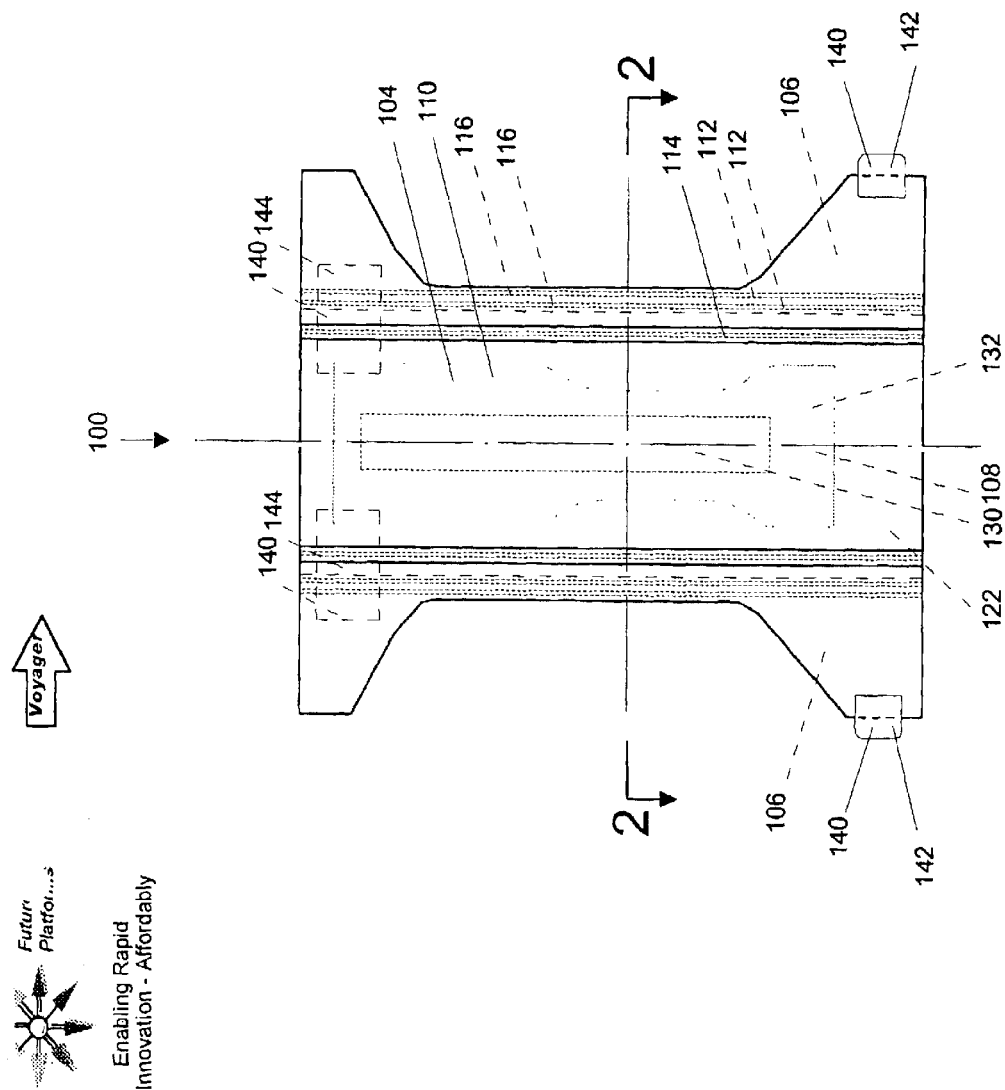
FIG. 1 is a plan view of an exemplary diaper, which can be produced by the production line of the present invention; shown in a flat-out state, wherein the wearer-facing side of the diaper is oriented towards the viewer.

The present invention reduces or eliminates the need for packing and transporting the webs (e.g., rolls of webs) from a web-producing facility to a web-converting facility producing disposable absorbent articles. The present invention includes a web-forming technology, in particular a non-woven technology, in a continuous, production line process of making disposable absorbent articles. The present invention includes a recycling technology for recycling non-woven materials on the production line of the present invention and re-using the recycled materials in the production of disposable absorbent articles of the present invention.

Terminology

A "disposable absorbent article" refers herein to a device that normally absorbs and retains fluids. In certain instances, the phrase refers herein to devices that are placed against or in proximity to the body of the wearer to absorb and contain the excreta and/or exudates discharged from the body, and includes such personal care articles as baby diapers, baby training pants, adult incontinence articles, feminine hygiene articles, baby swim diapers, wound dressing, and the like. In other instances, the phrase refers herein to protective articles, such as, for example, dining bibs that have the ability to absorb food items to prevent staining of the wearer's clothing. In still other instances, the phrase refers herein to devices that can retain a benefit component—such as a lotion, shampoo, soap, polishing material or cleansing material—until such time when the article is utilized by a consumer for its intended purpose. Such devices can include wash cloth, body wipes, body wraps, pet grooming articles, cleaning and polishing articles and the like.

The term "disposable" is used herein to describe products which generally are not intended to be laundered or otherwise restored or extensively re-used in their original function, i.e., preferably they are intended to be discarded after about 10 uses or after about 5 uses or after about a single use. It is preferred that such disposable articles be recycled, composed or otherwise disposed of in an environmentally compatible manner.

The term "diaper" refers herein to disposable absorbent articles generally worn by infants and other incontinent persons about the lower torso, and includes baby diapers, baby training pants, baby pool diapers, adult incontinence articles and the like.

The term "feminine hygiene articles" refers herein to any absorbent article worn by women to absorb and contain menses and other vaginal exudates.

A "body wrap" refers herein to an article or a garment worn about the body, typically to provide some therapeutic benefit, such as, for example, pain relief, wound coverage or to hold another device or article near the body.

The term "web" is meant herein any continuous material, including a film, a non-woven fabric, a foam or a combination thereof, or a dry lap material including wood pulp, and the like, having a single layer or multiple layers.

The term "non-woven material" refers herein to a material made from continuous and/or discontinuous fibers, without weaving or knitting by processes such as spun-bonding and melt-blowing. The non-woven material can comprise one or more layers, wherein each layer can include continuous or discontinuous fibers.

The term "film" refers herein to any polymeric film suitable in production of disposable articles, including breathable films.

The term "elastic" refers herein to any material that upon application of a force to its initial, relaxed, length can stretch or elongate to its elongated length without rupture and breakage, and which can substantially recover its initial length upon release of the applied force.

The term "polymeric material" refers herein to any thermosetting and thermoplastic materials, including compositions, blends and copolymers. The term "polymeric material" can also include various pigments to provide desired colors and/or visual effects.

The term "virgin polymeric material" or "virgin material" refers herein to materials that have been originally produced and have not been recycled for a secondary use.

The term "extrude" or "extruding" refers herein to a process by which a heated polymer is forced through one or more orifices or slots of a die to form a molten stream.

The term "bulk starting polymeric material" or "starting material" refers herein to any bulk polymeric material suitable in production of disposable absorbent articles or a component of a disposable absorbent article. The starting material can be provided in a bulk form including solids, semisolids, or solutions of one or more polymeric materials. In the solid form, the starting material can be supplied as pellets, granules or particles. The starting polymeric material can be a virgin polymeric material, a recycled polymeric material or a combination thereof.

A "spun-bonded module" refers herein to a machine capable of producing a molten stream of a polymeric material in a form of continuous fibers.

The term "melt-blown module" refers herein to a machine capable of producing a molten stream of a polymeric material in a form of discontinuous fibers.

The term "discontinuous fibers" or "melt-blown fibers" refers herein to limited-length strings normally produced by fragmenting one or more continuous fibers by a stream of hot gas and having a length ranging from about 5 mm to about 500 mm and a diameter less than about 20 microns.

The term "outage," or "interruption" refers herein to a production condition on the production line of the present invention when the continuous production process is interrupted by any malfunction of any of the converting operations and/or web-forming operations resulting in production of defective products.

Exemplary Disposable Absorbent Article

Figure 2:
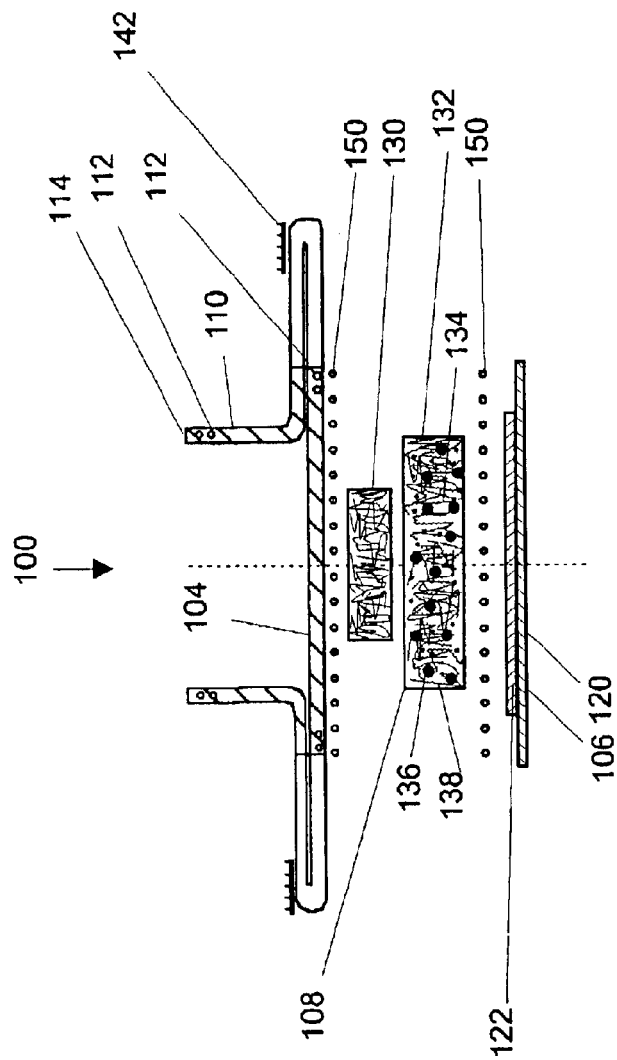
FIG. 2 is a cross-sectional view of the diaper in FIG. 1 taken along the cut line 2—2.

One example of a disposable absorbent article that can be produced by the production line of the present invention is illustrated in FIGS. 1 and 2. The diaper 100 preferably includes a liquid-permeable topsheet 104, a liquid-impermeable backsheet 106 opposing the topsheet 104, and an absorbent core 108 disposed therebetween. The topsheet 104 of the disposable absorbent article 100 contacts the skin of a wearer and allows bodily fluids penetrate through the topsheet 104 into the absorbent core 108. The topsheet 104 can be made of a composite material including a non-woven sheet to provide passage for the bodily fluids, elastic strands affixed to the non-woven sheet to provide a better fit around the body of the wearer (including legs, waist or whole lower torso), or any other feature suitable to provide better association of the topsheet 104 with the wearer's skin. The topsheet 104 of the diaper 100 preferably includes a non-woven sheet 110 and elastic strands 112 forming elasticized barrier leg cuffs 114 and leg elastics 116 to provide leakage protection around the wearer's legs. The topsheet 104 is preferably folded to form the elasticized barrier leg cuffs 114 including elastics 112.

The backsheet 106 prevents the body fluids to leak through. The backsheet 106 can be made of a composite material including a non-woven sheet 120 and a breathable film 122. The non-woven sheet 120 provides preferably both a cloth-like appearance of the outer layer of the diaper 100 and a fastening means for a hoop-and-loop fastening system. The breathable film 122 provides comfort to the wearer and resistance to the bodily liquids. The backsheet 106 can include any other material or feature suitable to provide a desired benefit.

The absorbent core 108 absorbs and retains the bodily fluids. The absorbent core 108 can include any suitable material capable of suspending and separating individual super absorbent particles (SAP) inside the absorbent core. The absorbent core 108 can have a single-piece or a multi-piece construction, wherein each construction piece is intended to perform a specific function in affecting or managing the bodily liquids. The absorbent core 108 of the diaper 100 preferably includes a two-piece construction: an acquisition core 130 for rapid acquisition of bodily liquids and a storage core 132 for storing the fluids inside the core 108. The acquisition core 130 is preferably a non-woven material having an open structure to facilitate rapid penetration of a flush of fluids through the structure. The storage core 132 is preferably a combination of a non-woven material 134 and SAP 136, which particles are preferably attached to the fibers 138 of the non-woven material 134 in order to suspend and separate the particles 136 inside the storage core 132.

The diaper 100 preferably includes a fastening system to hold the diaper 100 around the lower torso of the wearer. The fastening system can include any suitable fasteners, for example, tape fasteners or a hook-and-loop fasteners. The diaper 100 of the present invention preferably includes a hook-and-loop fastening system 140, which includes hook portions 142 attached to the topsheet 104, and a loop portion 144 comprised of non-woven fibers of the non-woven material 120 of the backsheet 106.

The topsheet 104 is preferably joined to the backsheet 106 and the absorbent core 108 of the diaper 100 by a bonding material 150, which can be provided in any suitable form, for example, as continuous or discontinuous fibers, beads, spirals, spots, or coated layers. It should be noted, however, that the components of the diaper 100 can be joined alternatively or in combination by any joining means known in the art, for example, heat bonds, pressure bonds, ultrasonic bonds, dynamic mechanical bonds, or any other suitable attachment means or combinations of these attachment means.

Production Line—First Embodiment

Figure 3:
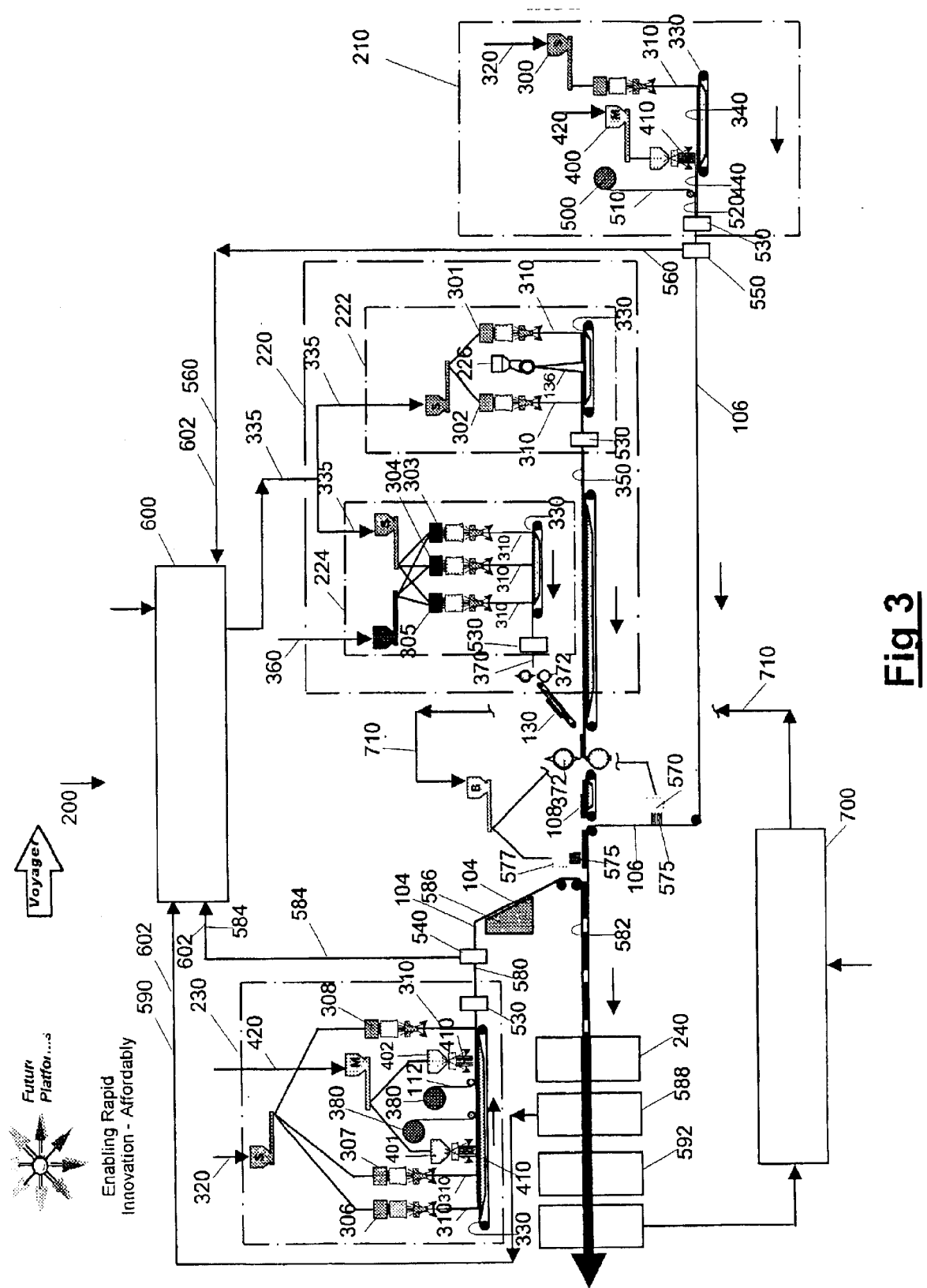
FIG. 3 is a material process flow diagram of one embodiment of the production line of the present invention for producing disposable absorbent articles.

FIG. 3 illustrates a material process flow diagram of one embodiment of a production line 200 of the present invention for producing disposable absorbent articles—in particular, the diaper 100 shown in FIGS. 1 and 2—from bulk polymeric materials. The bulk polymeric materials include both virgin polymeric materials and recycled polymeric materials. The production line 200 preferably includes a backsheet station 210, a core station 220 and a topsheet station 230 for providing, respectively, the backsheet 106, the absorbent core 108, and the topsheet 104.

Backsheet Station

Referring to FIG. 3, the backsheet station 210 can include any suitable number of spun-bonded modules 300 for providing continuous fibers, and/or melt-blown modules 400 for providing discontinuous fibers, and/or film modules 500 for providing continuous films. The spun-bonded modules 300, the melt-blown modules 400, and the film modules 500 can be disposed in any desirable order in relation to each other. FIG. 3 illustrates one embodiment of the backsheet station 210 including the spun-bonded module 300 for providing continuous fibers 310, the melt-blown module 400 for providing discontinuous fibers 410, and the film module 500 for providing a continuous film 510.

The spun-bonded module 300 and the melt-blown module 400 can be manufactured using any suitable conventional hardware normally used in production of non-woven materials and produced by such suppliers as, for example, Asson Engineering Inc., Florida 33301; Hills, Fla. 32904; Reifenhauser, Germany; JM Laboratories of Nordson, Ga., 30534; and Kobelco, Japan. The film module 500 can utilize any suitable hardware commonly used in production of disposable absorbent articles for feeding continuous webs from a supply roll or a festooned box.

The spun-bonded module 300 is provided with a bulk starting polymeric material 320, which can be any suitable virgin polymeric material, such as, for example, a spun-bonded 35 MFR polypropylene. The material 320 is converted in the spun-bonded module 300 into continuous spun-bonded fibers 310 that are then deposited onto a moving surface 330 to form a first layer 340.

The moving surface 330 can be any suitable surface including a screen; a perforated belt; a woven belt; a non-woven belt; one or more layers of spun-bonded fibers, melt-blown fibers or combination thereof, a porous film; or any combination thereof. The moving surface 330 can have any suitable shape, for example, flat, round, concave or convex. The moving surface 330 can include protrusions or projections, cavities or depressions, or any combination thereof. The moving surface 330 preferably includes openings that can be of any suitable size and shape to provide an open area sufficient for a blown gas (normally accompanying the production of non-woven materials) to flow at least partially through the openings, while the fibers are prevented to flow through the openings.

The melt-blown module 400 is provided with a bulk polymeric starting material 420, which can be any suitable virgin polymeric material, such as, for example, a melt-blown blown 1200 MFR polypropylene. The material 420 is converted in the melt-blown module 400 into discontinuous melt-blown fibers 410 that are then deposited preferably onto the first layer 340 to form a second layer 440.

The film module 500 is provided with a film 510, which is preferably a virgin film, i.e. a film produced from virgin, i.e., un-recycled, polymeric materials. The film 510 can be any polymeric film, preferably a breathable film suitable as a backsheet for disposable absorbent articles. The film 510 is deposited onto the second layer 440 to form a material 520, which is then forced through a consolidating device 530 to produce the backsheet 106 having a desired thickness and density.

The consolidating device 530 provides thermal bonds between adjacent fibers of a consolidating material and also between the non-woven fibers and the film 510 contacting the fibers, by applying heat, pressure or a combination of heat and pressure. The consolidating device 530 also forms a desired thickness of the consolidated material. The consolidating device 530 can include a contacting or non-contacting consolidating means. The contacting means can include, for example, calendaring rolls having smooth or textured surface(s), which come in a physical contact with the material. The non-contacting means can include, for example, hot gas or air, steam, vacuum and the like or any combination thereof.

After the consolidation device 530, the side edges of the backsheet 106 are preferably slit longitudinally by any suitable slitting device 550 to form a desired lateral dimension of the backsheet 106. A backsheet side-trim 560 is then preferably recycled on the production line 200 by a first recycling station 600 producing a first recycled polymeric material 335 that can be used in formation of the absorbent core 108. The recycling station 600 is described in detail herein below.

The backsheet 106 then passes a first bonding station 570 depositing a bonding material 575 onto the backsheet 106.

The bonding station 570 can be any suitable apparatus capable of producing a desired bonding pattern of a molten stream of polymeric material. The bonding pattern can include continuous or discontinuous fibers, beads, spirals, spots, or coated layers.

The bonding material 575 can be a second recycled polymeric material used on the production line 200. The bonding material 575 is produced by a second recycling station 700 described in detail herein below. After the application of the bonding material 575 on the backsheet 106, the backsheet 106 is combined with the absorbent core 108 and with the topsheet 104.

Core Station

Referring again to FIG. 3, the core station 220 can include any suitable number of core substations to provide any suitable single-piece or multi-piece construction of the absorbent core 108. In one embodiment shown in FIG. 3, the core station 220 includes a storage core substation 222 for providing the storage core 132 of the diaper 100 and an acquisition core substation 224 for providing an acquisition core 130.

The storage core substation 222 and the acquisition core substation 224 can include any suitable number of spun-bonded modules 300 or melt-blown modules 400, both described herein above. The storage core substation 222 can also include any number of SAP modules 226 for providing preferably a distributed flow of super absorbent particles 136 (SAP). The spun-bonded modules 300, the melt-blown modules 400 or the SAP modules 226 can be disposed in any suitable arrangement to provide a desired formation of the layers of the absorbent core 108.

The storage core substation 222 preferably includes two spun-bonded modules 300, denoted by numerals 301 and 302, separated by the SAP module 226 therebetween. The spun-bonded modules 301 and 302 are preferably provided with the first recycled polymeric material 335 (described herein below) to form continuous fibers. The spun-bonded module 301 deposits continuous fibers 310 onto the moving surface 330 described herein above. A consolidating device (not shown, but described herein above) forms a layer of continuous fibers having a desired thickness and thermal bonds between adjacent fibers. Then the SAP module 226 deposits the SAP material 136 onto the layer of continuous fibers, which is then covered by another layer of continuous fibers exiting the spun-bonded module 302. The resulting composite material undergoes a consolidation step by the consolidation device 530 (described herein above) forming a storage material 350 having a desired thickness and density.

The acquisition core substation 224 preferably includes three spun-bonded modules 300 (described herein above) denoted by numerals 303, 304 and 305. These modules preferably form bi-component fibers made of two different polymeric materials provided to the modules as separate material streams: a first stream 335 and a second stream 360. In one embodiment of the present invention, the first stream 335 is preferably the recycled polymeric described herein below, and the second stream 360 is preferably a virgin spun-bonded polyester. (It should be noted, however, that the recycled stream 335 can replace all or part of any virgin bulk starting polymeric material, for example, the virgin bulk starting polymeric material 320 used in the backsheet station 210, described herein above, and/or in the topsheet station 230, described herein below.)

The spun-bonded module 303 of the acquisition core substation 224 preferably deposits continuous fibers 310 onto the moving surface 330 (described herein above)

forming a first layer of continuous fibers. The spun-bonded module 304 deposits continuous fibers 310 onto the first layer of continuous fibers forming a second layer of continuous fibers. Then the spun-module 305 deposits continuous fibers 310 onto the second layer of continuous fibers forming a third layer of continuous fibers. The resulting material including the above three layers then undergoes a thermal treatment in the consolidating device 530 (described herein above) to form bonds between adjacent fibers at a very little pressure in order to preserve an open structure between the fibers and to form a desired structure of an acquisition material 370. The acquisition material 370 is then severed laterally by any suitable cutting device 372 to form the acquisition core 130 having a desired longitudinal dimension. The acquisition core 130 is then deposited on top of the storage material 350, which is then severed laterally by any suitable cutting device 372 to form the absorbent core 108 of the diaper 100.

The absorbent core 108 is then preferably deposited on top of the backsheet 106 and passed through a second bonding station 577 (described herein above) depositing the bonding material 575 onto the absorbent core 108. The bonding material 575 can be deposited at any desirable pattern described herein above. As described herein above, the bonding material 575 preferably includes a recycled polymeric material produced on the production line 200, which recycling operation is described in detail herein below. After the application of the bonding material 575 on the absorbent core 108, the absorbent core 108 is combined with the topsheet 104 to form a continuous laminate 582.

Topsheet Station

Referring again to FIG. 3, the topsheet station 230 can include any suitable number of spun-bonded modules 300 to provide continuous fibers and/or melt-blown modules 400 to provide discontinuous fibers. The spun-bonded modules 300 and the melt-blown modules 400 can be disposed in any desired order in relation to each other. The topsheet station 230 can also include any suitable number of elastic strand devices, wherein each elastic strand device can provide any desired number of elastic strands. In one embodiment shown in FIG. 3, the topsheet station 230 preferably includes three spun-bonded modules 300, denoted by numerals 306, 307, and 308; two melt-blown modules 400, denoted by numerals 401 and 402; and two elastic strand devices 380, each providing preferably two elastic strands 112. The elastic strand device 380 can be any device suitable for feeding a desired number of continuous elastic strands simultaneously at a desired, preferably variable speed, to form preferably a differential stretch profile in the elastic strands 112.

The spun-bonded modules 306, 307 and 308 are preferably provided with the bulk starting material 320 (described herein above), and the melt-blown modules 401 and 402 are preferably provided with the bulk starting material 420 (described herein above). The spun-bonded module 306 deposits continuous fibers 310 onto the moving surface 330 (described herein above) forming a first layer of continuous fibers. The spun-bonded module 307 deposits continuous fibers 310 onto the first layer of continuous fibers to form a second layer of continuous fibers. Then the melt-blown module 401 deposits discontinuous fibers 410 onto the second layer of continuous fibers to form a first layer of discontinuous fibers. After that, each of the elastic strand stations 380 deposits elastic strands 112 onto the second layer of discontinuous fibers, which are then covered by a second layer of discontinuous fibers 410 deposited by the melt-blown module 402. Finally, the spun-bonded module 308 deposits continuous fibers 310 onto the second layer of discontinuous fibers to form a composite material, which is then passes the consolidating device 530 (described herein above) to form a desired topsheet 104 having a desired thickness and density.

After the consolidation device 530, the side edges of the topsheet 104 are preferably slit or cut longitudinally by any suitable cutting device 540 to form a desired lateral dimension of the topsheet 104. The produced topsheet side-edge trim 584 is then preferably recycled on the production line 200 by the first recycling station 600 producing the first recycled polymeric material 335 used in the formation of the absorbent core 108. The first recycling station 600 is described in detail herein below.

After slitting, the topsheet 104 is preferably folded by any suitable folding device 586 to form a desired folded configuration of the topsheet 104, which is then deposited on top of the absorbent core 108 to form the continuous laminate 582. The continuous laminate 582 is then preferably undergoes a side-notch-cutting operation 588 to form a desirable lateral configuration of the continuous laminate 582 to provide a desired configuration in the crotch area of the diaper 100. A side-notch trim 590 resulting from the side-notch-cutting operation 588 is preferably recycled on the production line 200, together with the backsheet side trim 560 and the topsheet side trim 584, by the first recycling station 600 producing the first recycled polymeric material 335.

Other Operations

Referring again to FIG. 3, other operations on the production line 200 preferably include an application of the fastening hook material 142 provided by a fastening module 240; the final knife operation 592 for severing the continuous laminate 582 into individual diapers 100; folding and packaging individual diapers 100 into any suitable size and shape packages containing any desired number of diapers.

First Recycling Station

Referring again to FIG. 3, the production line 200 preferably includes the first recycling station 600 for collecting and recycling a side-trim 602 collected during a normal operation of the production line 200 into the first recycled polymeric material 335 for a re-use on the production line 200, preferably in production of the absorbent core 108 of the diaper 100. The side trim 602 can include the backsheet side-trim 560 collected from cutting the side edges of the backsheet material; the topsheet side-trim 584 collected from cutting the side edges of the topsheet 104; and separate pieces of webs comprising a side-notch trim 590 collected from cutting side-notch pieces from the combined laminate 582. The side-trim 602 can be collected off the moving surface 330 by any suitable conventional means, including a suction means conveying the collected trim through a piping system.

Figure 4:
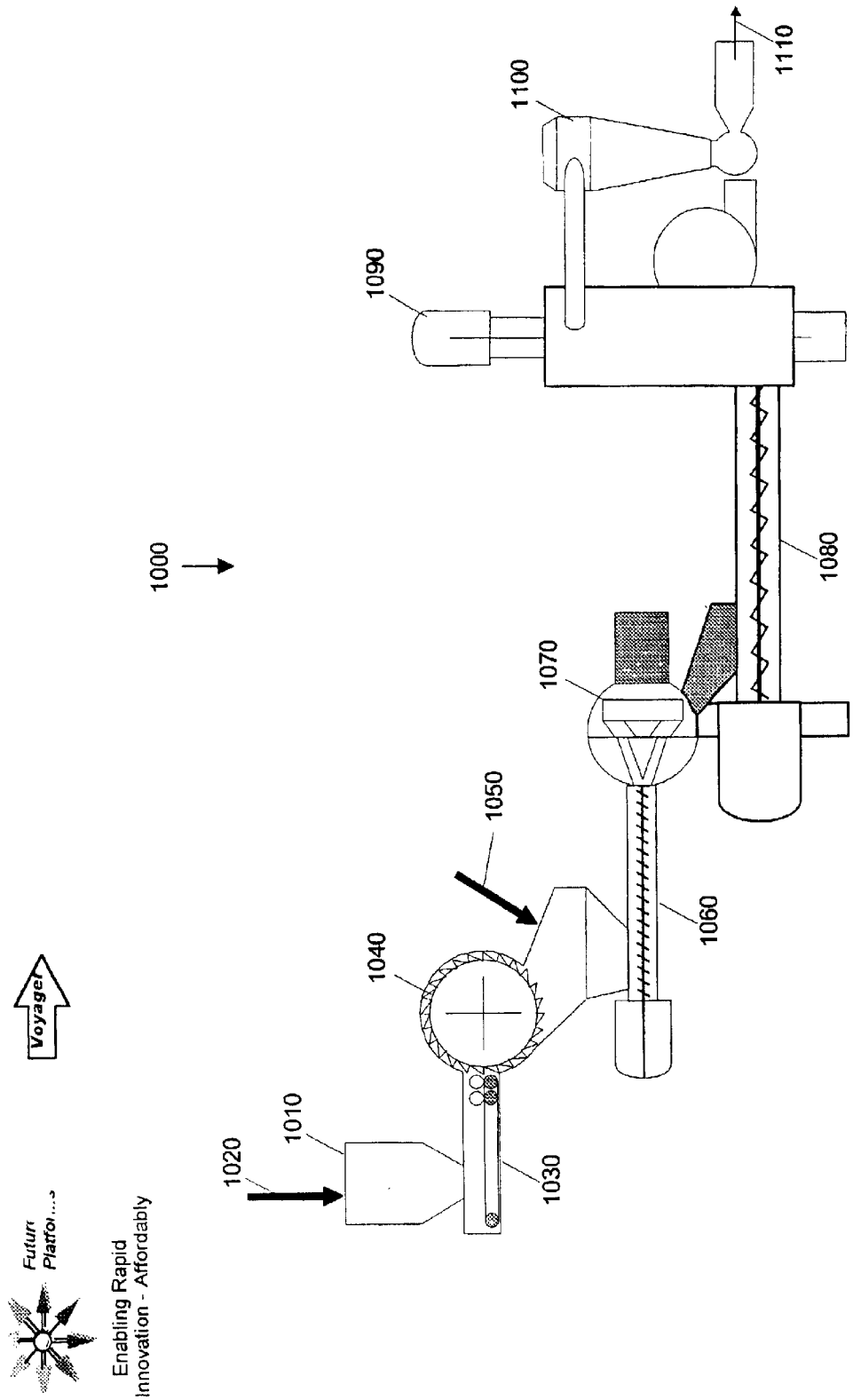
FIG. 4 illustrates a schematic diagram of a recycling station including in the production line shown in FIG. 3.

The first recycling station 600 can be any suitable conventional recycling operation including preferably the following process steps: collecting the side trim; shredding the side trim; mixing the shredded material with an additive material that can be any desired material intended to provide and maintain desired properties of the recycled material, melting the mixed material into a molten stage, extruding and forming pellets of recycled polymeric material, cooling and drying the pellets. Suitable recycling systems can be obtained from such companies as, for example, Artec of Austria, Zuiko of Japan, Ibis of Georgia and Osprey of Georgia FIG. 4 illustrates a schematic diagram 1000 of the first recycling station 600 of the present invention, which includes a hopper 1010 for feeding the collected material 1020 into a conveyor 1030 (preferably having a metal detecting device) for feeding into a shredder 1040 capable to accept an additive material 1050 to form a mixed material. The mixed material is then melted in the extruder 1060 and formed into pellets by a pelletizer 1070 feeding the pellets into a cooler 1080 and a drier 1090, which discharges the cooled, dried pellets of the recycled polymeric material 1110 through a cyclone device 1100.

Second Recycling Station

Referring back to FIG. 3, the production line 200 further preferably includes a second recycling station 700 for collecting and recycling the non-woven materials collected during the outages of the production line 200. The term "outage," or "interruption" refers herein to a production condition on the production line of the present invention when the continuous production of diapers 100 on the line 200 is interrupted by any malfunction of any of the converting operations and/or the web-forming operations resulting in production of defective products.

During the outage of the production line 200, the converting operations are interrupted, but the nonwoven-web forming operations of the spun-bonded modules 300 and the melt-blown-modules 400 preferably continue uninterrupted in order to avoid undesired solidification of molten polymeric materials inside the nonwoven-forming equipment. The outages also include situations when one or more of the nonwoven-forming modules are malfunctioning and their operation needs to be interrupted, however, the remaining nonwoven-forming modules continue to extrude the materials for collecting, recycling and re-use on the production line of the present invention.

The collected materials can include the backsheet 106, the topsheet 104, the storage core material 350 and/or the acquisition core material 370. The materials can be collected off the moving surface by any suitable conventional means. It is preferred that the nonwoven materials collected for recycling on the production line 200 do not include other, undesirable materials. For example, the collected for recycling the backsheet 106 preferably does not include the film 510; the storage core material 350 preferably does not include the SAP material 136, and the topsheet material 586 preferably does not include elastic strands 112. Therefore, it is preferred that during the outages on the line 200, the process operations for supplying the film 510, the SAP material 136 and the elastic strands 112 are interrupted. (It should be noted that nonwoven materials including the above-undesired materials are preferably not intended for recycling on the production line of the present invention and can be discharged as scrap materials.)

The second recycling station 700 preferably recycles the collected non-woven materials into a second recycled material 710 that can be re-used on the production line as a bonding material to bond together the topsheet 104, the backsheet 106, and the absorbent core 108. (It should be noted, however, that the second recycled material 710 can replace all or part of any virgin bulk starting polymeric material, for example, the virgin bulk starting polymeric material 320 used in the backsheet station 210 and/or in the topsheet station 230, described herein above.)

The second recycling station 700 can be any suitable commercial recycling system, for example, the first recycling station 600 illustrated as the schematic diagram 1000 in FIG. 4. If desired, the additive material 1050 can be any suitable material including tackyfying materials for providing a desired tacky property and/or elasticizing materials for providing a desired elastic property of the recycled bonding material 710.

Production Line—Second Embodiment

Figure 5:
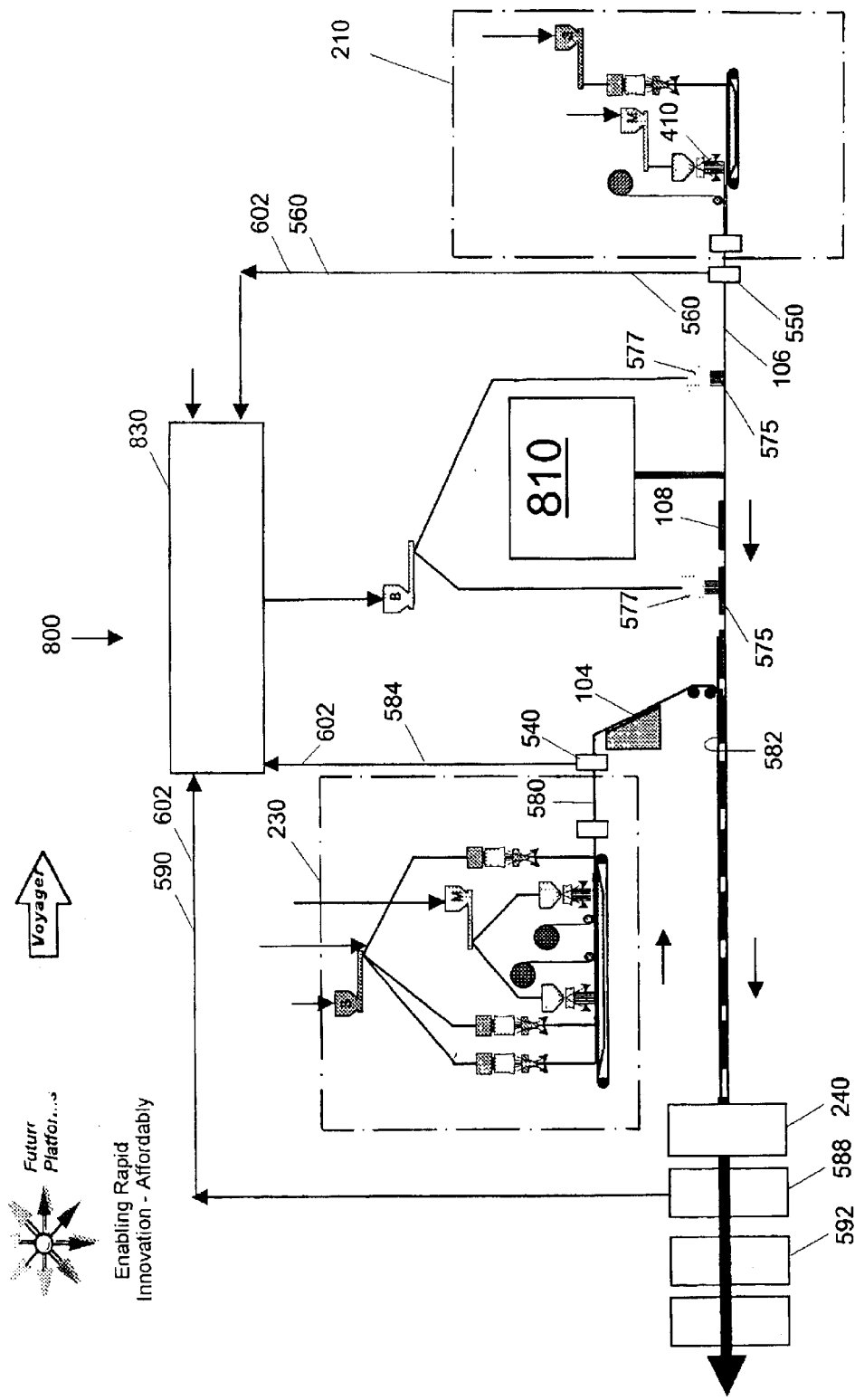
FIG. 5 is a material process flow diagram of another embodiment of the production line of the present invention for producing disposable absorbent articles.

FIG. 5 shows a schematic diagram of a second embodiment of a production line 800 of the present invention. The production line 800 is one of the variations of the production line 200, wherein the core station 220, forming the core 108 on the line 200, is substituted by a core station 810 capable of providing the absorbent core 108 to the production line 800 as a material produced off-line, i.e., off the production line 800, in a form of a continuous web or discrete pieces (for example, the acquisition core 130 and the storage core 132 can be provided as one or more continuous webs or separate pieces made off the production line 800). The core station 810 can be any suitable conventional material-feeding systems for feeding continuous webs or discrete objects into a high-speed converting process for manufacturing disposable absorbent articles.

The production line 800 preferably includes a recycled station 830 for recycling the side-trim 602 (described herein above) collected preferably during normal operations of the production line 800, as well as nonwoven materials of the backsheet 106 and the topsheet 104 collected during the outages of the production line 800. (Similarly to the production line 200, described herein above, the production of the backsheet 106 and the topsheet 104 can continue uninterrupted on the production line 800.).

During the outages of the line 800, the operation of the core station 810 supplying the core 108 is interrupted in addition to the interrupted operations for supplying the film 510 and the elastic strands 112. The recycled station 830 preferably recycles the collected non-woven materials into the bonding material 575 (described herein above), which represents a re-use of the recycled non-woven materials collected from the line 800. The recycling station 830 can be any suitable commercial recycling system, for example, the first recycling station 600 illustrated as the schematic diagram 1000 in FIG. 4.

Spun-Bonded Recycling System

Figure 6:
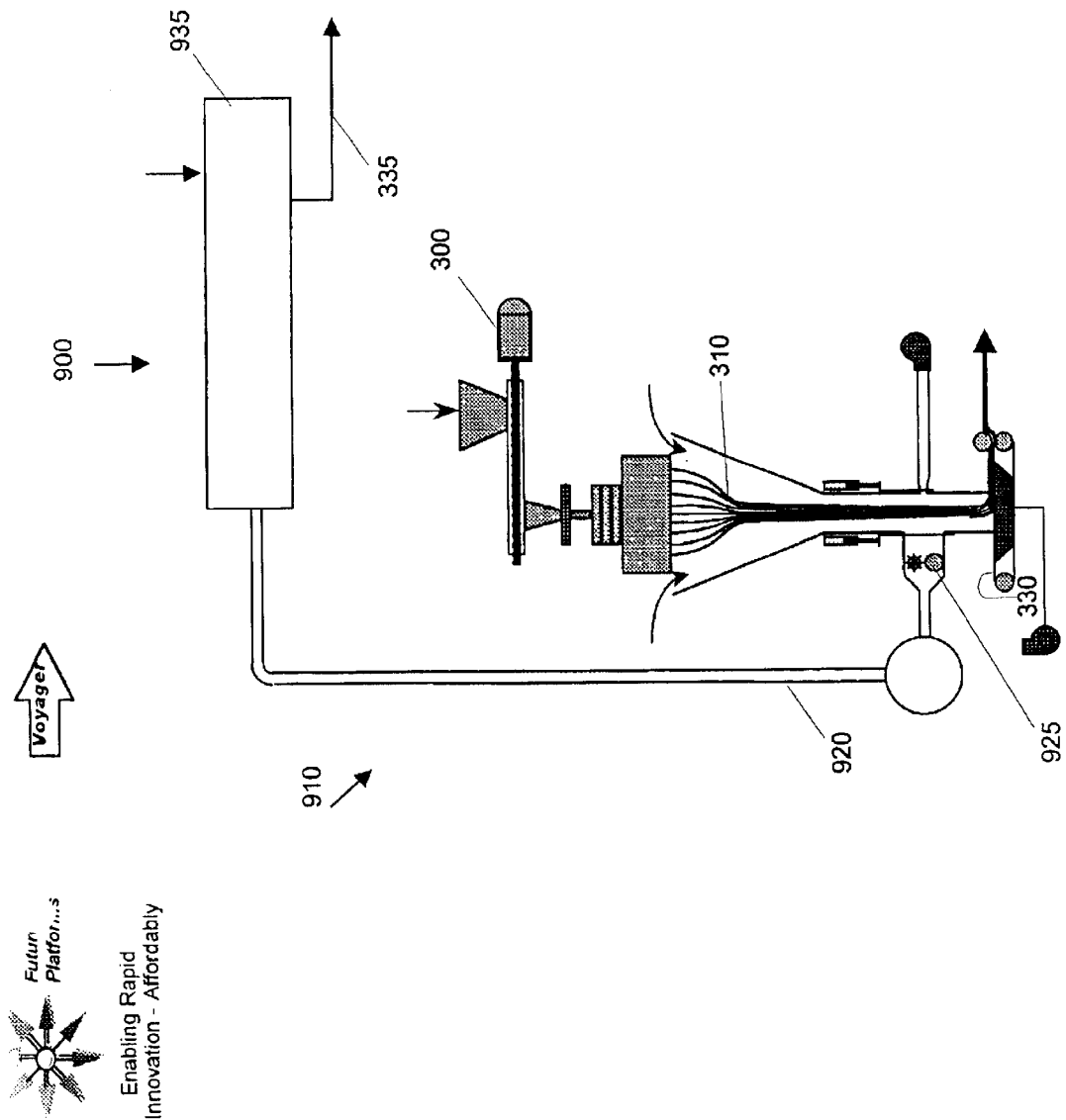
FIG. 6 is a schematic diagram of a spun-bonded recycling system of the present invention during a normal operation of the production line of the present invention.
Figure 7:
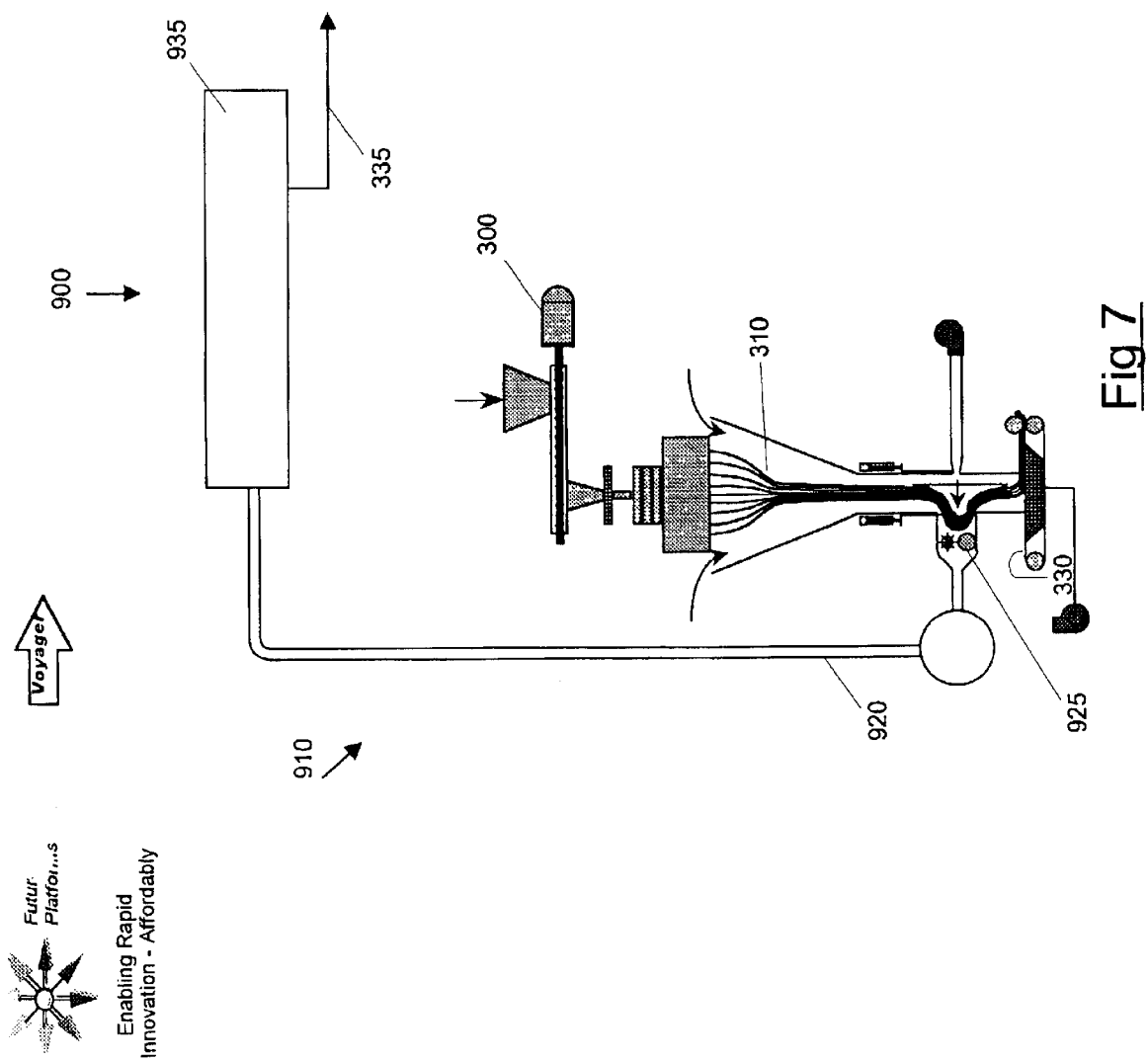
FIG. 7 is a schematic diagram of the spun-bonded recycling system shown in FIG. 5 at the beginning of an outage on the production line of the present invention.
Figure 8:
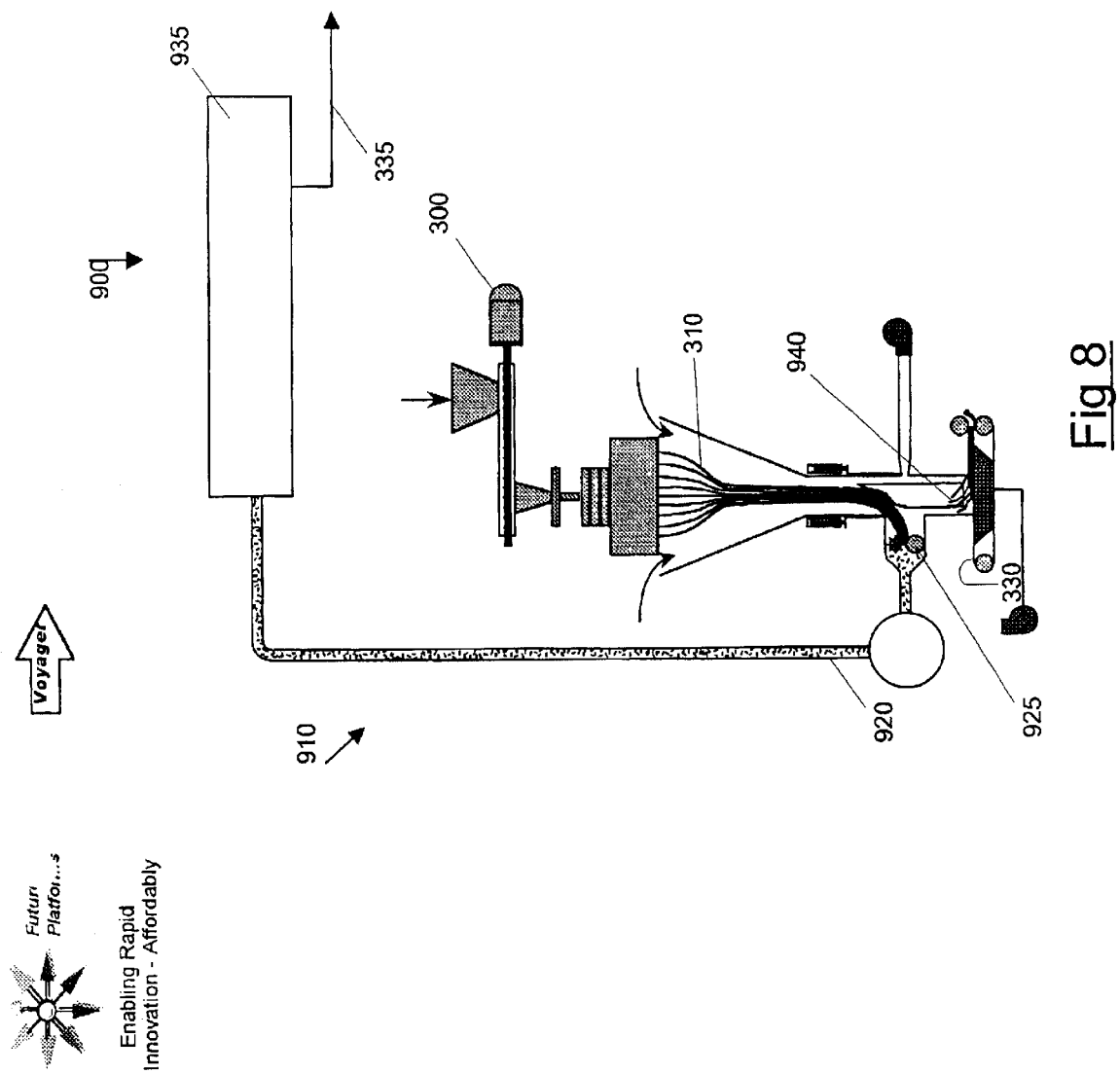
FIG. 8 is a schematic diagram of the spun-bonded recycling system shown in FIGS. 5 and 8 during an outage on the production line.

FIG. 6–8 show a schematic diagram of one embodiment of a spun-bonded recycling system 900, which is especially beneficial when the movement of the moving surface 330 needs to be interrupted and the flow of continuous fibers 310 needs to be diverted from the normal flow of depositing on the moving surface 330. The spun-bonded recycling system 900 preferably includes one or more spun-bonded modules 300 (described herein above) and a spun-bonded recycling operation 910. The recycling operation 910 re-uses the continuous fibers 310 produced by the spun-bonded module 300 during outages of the production line 200 or the production line 800, preferably when the movement of the moving surface 330 is interrupted.

FIG. 6 illustrates an operation of the spun-bonded recycling system 900 during a normal operation of the production line 200 when the continuous fibers 310 are produced by the spun-bonded module 300 and deposited on the moving surface 330, described herein above. FIG. 7 illustrates an operation of the spun-bonded recycling system 900 at a beginning of an outage of the production line of the present invention, when the continuous fibers 310 continue to be produced by the spun-bonded module 300 and when the moving surface 330 is stopped. At such an instance, the continuous fibers 310 can be diverted from their normal flow, collected and recycled on the production line of the present invention for a re-use on the production line of the present invention.

FIG. 7 illustrates the steps of diverting the flow of continuous fibers 310 from a normal production mode into a collection-and-recycling mode by a gust of a compressed liquid, (gas, air, fluids) to force the flow of continuous fibers 310 to divert into the recycling operation 910. FIG. 8 illustrates an operation of the spun-boned recycling system 900 during an outage in progress, when the diverted continuous fibers 310 can be disintegrated by a shredder 925 of the recycling operation 910 and conveyed through a pipe 920 (or any other suitable conventional means) into a recycling station 935 capable of producing the recycled starting polymeric material 335, described herein above. The recycling station 935 can be any suitable commercial recycling system, for example, the first recycling station 600 illustrated as the schematic diagram 1000 in FIG. 4.

As shown in FIG. 8, during the divergence of the continuous fibers 310 into the recycling mode, a tail 940 of disconnected fibers 310 is left on the surface 330, the movement of which can be interrupted during the outage if needed. After the outage is corrected, the moving surface 330 resumes its movement, and the continuous fibers 310 are deposited again onto the moving surface 330 for re-uniting with the tail 940 to form a continuous material flow preferably by the consolidating device 530 described herein above. The moving surface 330 resumes conveying the continuous fibers 310 to the downstream operations of the production line of the present invention.

Melt-Blown Recycling System

Figure 9:
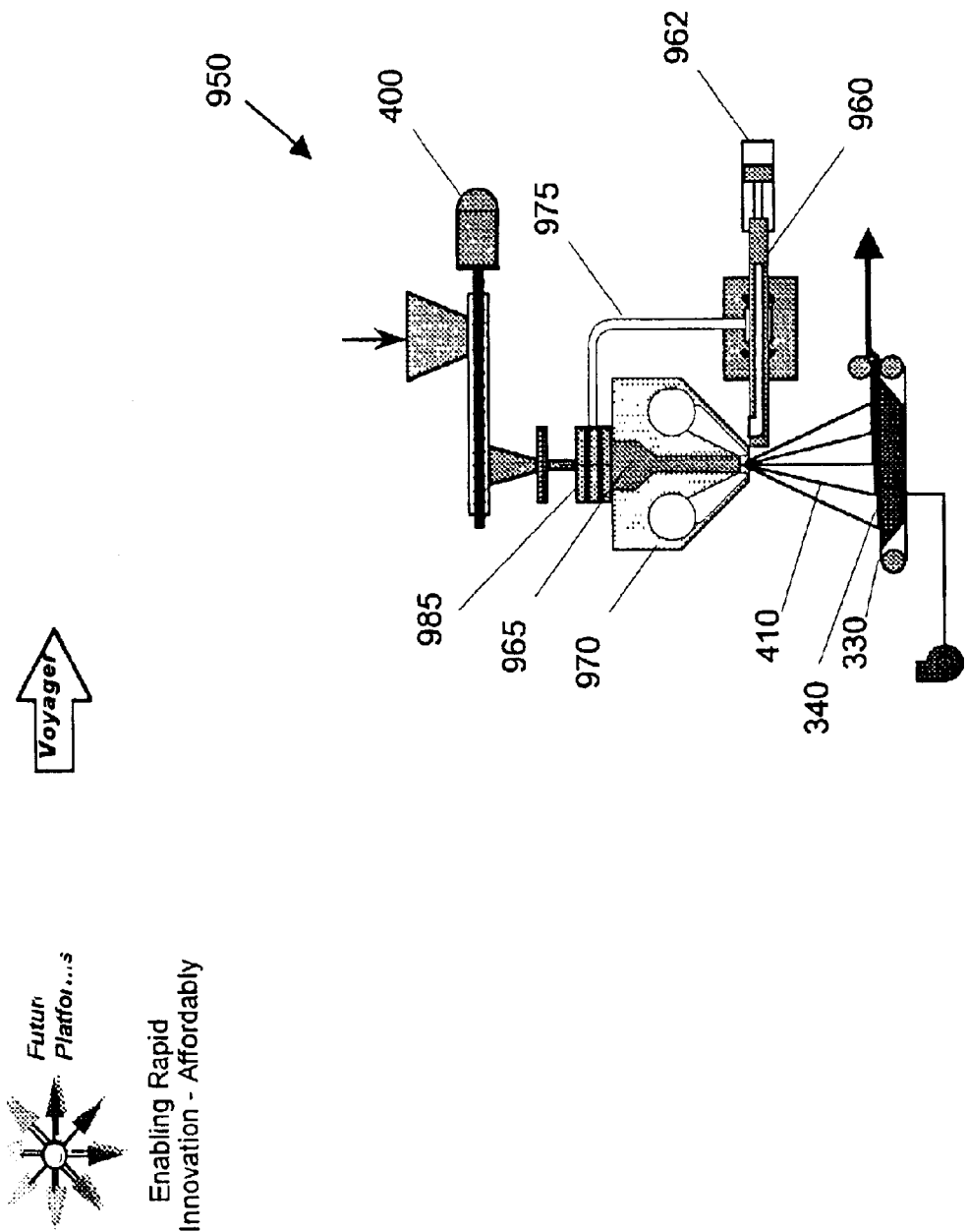
FIG. 9 is a schematic diagram of a melt-blown recycling system of the present invention during a normal operation on the production line of the present invention.
Figure 10:
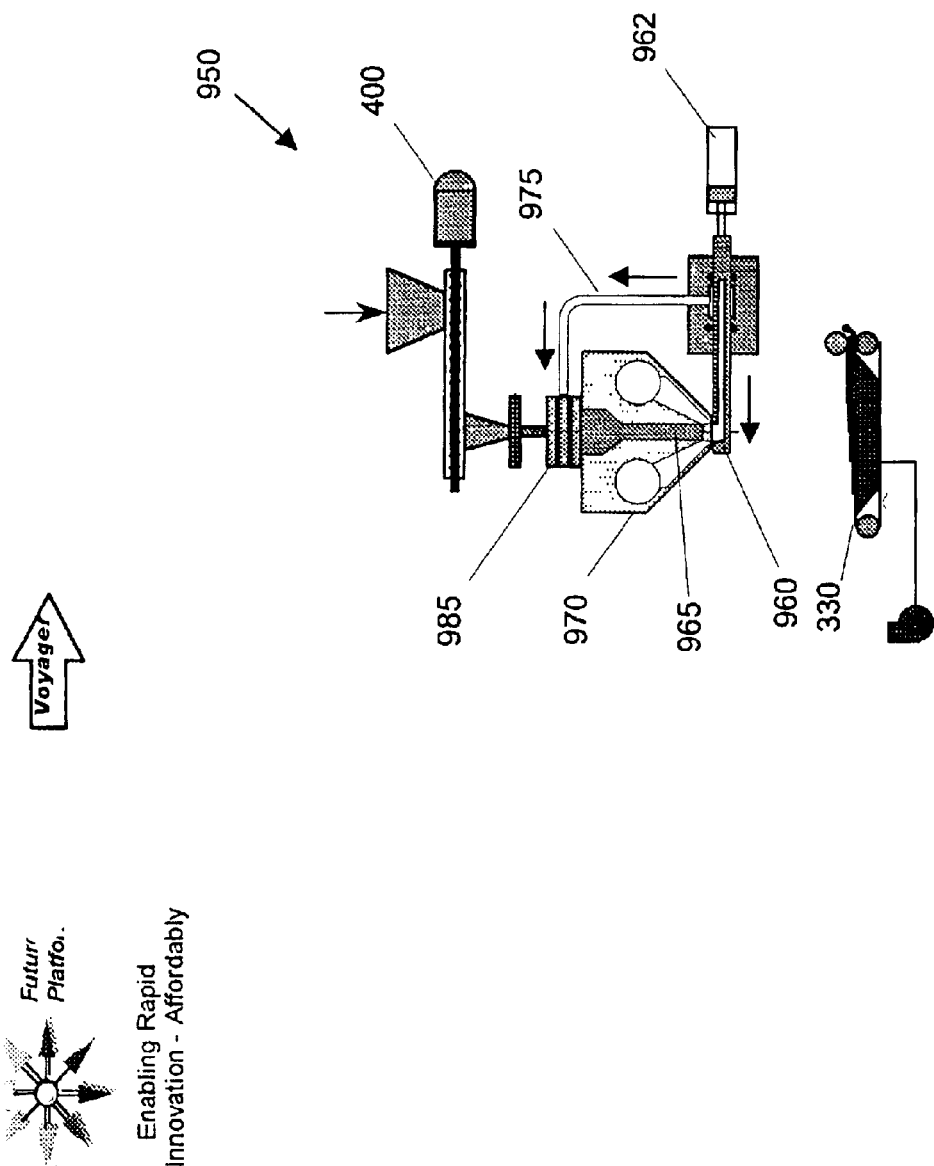
FIG. 10 is a schematic diagram of a melt-blown recycling system of the present invention during an outage on the production line of the present invention.

FIG. 9 shows a schematic diagram of a normal operation of the melt-blown module 400, described herein above, producing and depositing the melt-blown flow 410 onto the moving surface 330 to form the layer 340 of melt-blown material. FIG. 10 shows the operation of the melt-blown module 400 during an outage on the production line 200 or 800, in particular, when it is desired that the moving surface 330 be stopped. In such instances the melt-blown module 400 can recycle the extruded polymeric material using a melt-blown recycling system 950, one embodiment of which is shown in FIG. 10. The melt-blown recycling system 950 can include one or more melt-blown modules 400, each including a collecting die 960 actuated by a suitable actuating device 962 and capable of collecting a molten polymeric material 965 exiting the spinneret 970 of the melt-blown module 400. The collected molten material 965 is conveyed through a conduit 975 back into a metering pump 985 of the melt-blown module 400. The temperature inside the collecting die 960 and the conduit 975 is preferably maintained to prove a molten state of the polymeric material. A suitable conduit 975 can be a suitable heated pipe.

Single-Product-Lane and Multiple-Product-Lane Production Lines

The production line of the present invention can be a single-product-lane operation or a multiple-product-lane operation, for example, from 2 to 40 or more product lanes. For the economic reasons, in order to efficiently utilize the production capability of the non-woven technology of the spun-bonded modules 300 and the melt-blown modules 400, the preferred embodiment of the production line of the present invention includes a four-product-lane operation, wherein the produced materials can be slit into four product lanes forming any desirable configuration.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A production line for manufacturing disposable absorbent articles, the production line extruding a number of polymeric materials and forming from the extruded polymeric materials individual components of the disposable absorbent articles including a liquid pervious topsheet, a liquid impervious backsheet and an absorbent core disposed therebetween, the production line comprising:

a) a first moving surface to move a web of material through the production line;

b) a backsheet station adjacent the first moving surface to form the backsheet by extruding a first polymeric material onto the first moving surface, the first polymeric material being provided to the backsheet station as a first starting material, c) a core station adjacent the first moving surface to form the absorbent core by extruding a second polymeric material onto the backsheet, the second polymeric material being provided to the core station as a second starting material;

d) a second moving surface to move a web of material through the production line;

e) a topsheet station adjacent the second moving surface to form the topsheet by extruding a third polymeric material onto the second moving surface, the third polymeric material being provided to the topsheet station as a third starting material, the topsheet being placed onto the absorbent core;

f) one or more cutting devices adjacent the first and second moving surfaces to cut a side-trim to form lateral configurations of the topsheet or the backsheet;

g) a first recycling station for collecting and recycling the side-trim into a first recycled material;

h) a second recycling station for collecting and recycling non-woven materials of the topsheet, the backsheet or the absorbent core during an outage of the production line into a second recycled material;

i) one or more bonding modules adjacent the first and second moving surfaces to provide the second recycled material for bonding the backsheet or the topsheet; and j) a conduit for providing the second recycled material from the second recycling station to one or more of the bonding modules.

2. The production line of claim 1, wherein the first starting material comprises a first virgin material.

3. The production line of claim 1, wherein the first starting material comprises the first recycled material.

4. The production line of claim 1, wherein the first starting material comprises the second recycled material.

5. The production line of claim 1, wherein the second starting material comprises the first recycled material.

6. The production line of claim 1, wherein the second starting material comprises a second virgin material.

7. The production line of claim 1, wherein the third starting material comprises a third virgin material.

8. The production line of claim 1, wherein the third starting material comprises the first recycled material.

9. The production line of claim 1, wherein the third starting material comprises the second recycled material.

10. A production line for manufacturing disposable absorbent articles, the production line comprising:

(a) a first moving surface to move a web of material through the production line;

(b) a backsheet station adjacent the first moving surface to form a backsheet of the disposable absorbent article by extruding a first polymeric material onto the first moving surface, the first polymeric material being provided to the backsheet station as a first starting material;

(c) a second moving surface to move a web of material through the production line;

(d) a core station adjacent the second moving surface to provide an absorbent core produced off the production line and provided to the production line as a continuous web or discrete objects;

(d) a third moving surface to move a web of material through the production line;

(e) a topsheet station adjacent the third moving surface to form a topsheet of the disposable absorbent article by extruding a second polymeric material onto the third moving surface, the second polymeric material being provided to the topsheet station as a second starting polymeric material, the topsheet being placed onto the absorbent core;

(f) one or more cutting devices adjacent the first and third moving surfaces to cut a side-trim to form lateral configurations of the topsheet or the backsheet;

(g) a recycling station for collecting and recycling the side trim or non-woven materials of the topsheet or the backsheet collected during an outage on the production line into a recycled polymeric material;

(h) one or more bonding modules adjacent the first and third moving surfaces to provide the recycled material for bonding the backsheet or the topsheet; and (i) a conduit for providing the recycled material from the recycling station to one or more of the bonding modules.

11. The production line of claim 10, wherein the first starting material comprises a first virgin material.

12. The production line of claim 10, wherein the first starting material comprises the recycled material.

13. The production line of claim 10, wherein the second starting material comprises a second virgin material.

14. The production line of claim 1, wherein the second starting material comprises the recycled material.

* * * * *

UNITED STATES PATENT AND TRADEMARK OFFICE
CERTIFICATE OF CORRECTION

PATENT NO.    : 6,802,353 B2
DATED         : October 12, 2004
INVENTOR(S)   : Malakouti et al.

It is certified that error appears in the above-identified patent and that said Letters Patent is hereby corrected as shown below:

Column 2,
Line 23, delete "previous" and insert therefor -- pervious --.

Column 4,
Line 34, delete "composed" and insert therefor -- composted --.

Column 7,
Line 31, delete second occurrence of "blown".

Column 14,
Line 6, delete "topeheet" and insert therefor -- topsheet --.

Signed and Sealed this

Tenth Day of May, 2005

JON W. DUDAS
*Director of the United States Patent and Trademark Office*